United States Patent [19]

De Felippis et al.

[11] Patent Number: 5,952,297
[45] Date of Patent: Sep. 14, 1999

[54] MONOMERIC INSULIN ANALOG FORMULATIONS

[75] Inventors: Michael R. De Felippis; Bruce H. Frank, both of Indianapolis, Ind.

[73] Assignee: Eli Lilly and Company, Indianapolis, Ind.

[21] Appl. No.: 08/938,245

[22] Filed: Sep. 26, 1997

Related U.S. Application Data

[63] Continuation of application No. 08/414,880, Mar. 31, 1995, abandoned.

[51] Int. Cl.$^6$ .................................................. A61K 38/28
[52] U.S. Cl. ............................................. 514/3; 530/380
[58] Field of Search ................................. 530/380; 514/3

[56] References Cited

U.S. PATENT DOCUMENTS

| | | | |
|---|---|---|---|
| 2,626,228 | 5/1953 | Petersen | 167/75 |
| 2,648,622 | 8/1953 | Waugh et al. | 167/75 |
| 2,799,622 | 7/1957 | Schlichtkrull et al. | 167/75 |
| 2,819,999 | 1/1958 | Schlichtkrull et al. | 167/75 |
| 2,849,370 | 8/1958 | Petersen et al. | 167/75 |
| 2,882,202 | 4/1959 | Petersen et al. | 167/75 |
| 2,882,203 | 4/1959 | Petersen et al. | 167/75 |
| 2,920,014 | 1/1960 | Petersen et al. | 167/75 |
| 3,060,093 | 10/1962 | Poulsen et al. | 167/75 |
| 3,102,077 | 8/1963 | Christensen et al. | 167/75 |
| 4,476,118 | 10/1984 | Brange et al. | 424/178 |
| 5,070,186 | 12/1991 | Joergensen | 530/304 |
| 5,177,058 | 1/1993 | Dorschug | 530/304 |
| 5,461,031 | 10/1995 | De Felippis | 530/304 |
| 5,474,978 | 12/1995 | Bakayasa et al. | 530/304 |
| 5,504,188 | 4/1996 | Baker et al. | 530/304 |
| 5,514,646 | 5/1996 | Chance et al. . | |
| 5,534,488 | 7/1996 | Hoffmann | 530/304 |

FOREIGN PATENT DOCUMENTS

| | | |
|---|---|---|
| 539091 | 9/1984 | Australia . |
| 025 868 | 1/1981 | European Pat. Off. ........ A61K 37/02 |
| 0 214 826 | 3/1987 | European Pat. Off. .......... C07K 7/10 |

OTHER PUBLICATIONS

Smirn, Caplus # 1992:228393.
Liang, Caplus # 1995:171408.
Brange, Medline # 94290674, 1993.
Whimngham, Caplus # 1995:910948.
Frank, B.H., Self–Association and Conformational Studies on Human Proinsulin and Insulin Analogs (1990).
Skyler, Insulin Treatment, Therapy for Diabetes Mellitus and Related Disorders, American Diabetes Assoc., Alexandria, VA, 127–137 (1991).
Tattersall, Bovine Insulin, *BMJ*, 305, 831 (1992).
Seigler et al., Pharmacokinetics of long–acting (ultralente) insulin preparations, *Diabetes Nutrition & Metabolism*, 4, 267–273 (1991).
Graham et al., An in–vitro test for the duration of action in insulin suspensions, *J. Pharm. Pharmacol.* 36, 427–430 (1984).

Francis et al., Human Ultralete Insulin, *Diabetes Research*, 3, 263–268 (1986).

Freeman et al., Use of human ultralente as the basal insulin component in treatment of patients with IDDM, *Diabetes. Res. and Clin. Practice*, 12, 187–192 (1991).

Fontbonne, Insulin–A Sex Hormone for Cardiolvascular Risk, *Circulation*, 84, 1442–1444 (1991).

Owens et al., Human, Procine and Bovine Ultralente Insulin:Subcutaneous Adminstration in Normal Man, *Diabetic Medicine*, 3, 326–329 (1986).

Holman et al., Human Ultralente Insulin, *British Med. J.*, 288, 665–668 (1984).

Massey, et al., What Were Those Crystals? The Dissolution and Disintegration of Insulin, *JAMA*, 259:12, 1811–1812 (1988).

Hirsch et al., Intensive Insulin Therapy:Part I. Basic Principles, *Amer. Family Physician*, 45:5, 2141–2147 (1992).

Harding, et al., An Investigation of Rhombohedral Zinc Insulin Crystals and a report of Other Crystalline Forms, *The Crystal Structure of Insulin II*, 212–226 (1965).

Brems, et al., Improved insulin stability through amino acid substitution, *Protein Engineering*, 5:6, 519–525 (1992).

Brange, et al., Monomeric Insulins and Their Experimental and Clinical Implications, *Diabetes Care*, 13:9 923–954 (1990).

Jorgensen et al., NovoSol Basal:Pharmacokinetics of a Novel Soluble Long Acting Insulin Analogue, *BMJ*, 299, 415–419 (1989).

Hansen, The self–association of zinc–free human insulin and insulin analogue B13–glutamine, *Biophysical Chemistry*, 39, 107–110 (1991).

Kirk–Othmer, *Encyclopedia & Chemical Technology*, 3rd Ed. vol. 13, John Wiley and Sons, N.Y. 1981, pp. 607–614 (1980).

(List continued on next page.)

*Primary Examiner*—Cecilia J. Tsang
*Assistant Examiner*—Patrick R. Delaney
*Attorney, Agent, or Firm*—Mark J. Stewart; Steven P. Caltrider

[57] ABSTRACT

The present invention discloses various parenteral pharmaceutical formulations having a protracted effect, which comprise: a sterile aqueous suspension of about 20 U/mL to about 500 U/mL insulin analog, about 5 mg/mL to about 10 mg/mL sodium chloride, about 0.2 to about 2.0 mg/mL physiologically acceptable buffer, a zinc ion content of about 0.07 mg/mL to about 0.1 mg/mL, and a physiologically acceptable preservative at a pH of about 6.5 to about 7.8; such that less than 5% of the analog present in the suspension is in the dissolved state.

16 Claims, No Drawings

OTHER PUBLICATIONS

Home et al., Bioavailability of Highly Purified Bovine Ultralente Insulin, *Diab. Care*, 6:2, 210 (1983).

Owens, Long–acting Insulin Preparations, *Human Insulin Clinical Pharmacological Studies in Normal Man*, 170–177 (1986).

Dodson, et al., Insulin assembyl: its modification by protein engineering and ligand binding, *Phil. Trans. R. Soc. Lond. A*, 345, 153–164 (1993).

Brange, Galenics of Insulin: The Physico–chemical and Pharmaceutical Aspects of Insulin and Insulin Preparation, Springer–Verlag Berlin Heidelbert (1987).

Schlichtkrull, Chemical and Biological Studies on Insulin Crystals and Insulin Zinc Suspensions, Insulin Crystals (1958).

Hallas–Møller et al., Cystalline and Amorphous Insulin–Zinc Compounds with Prolonged Action, *Science*, 116, 394–398 (1952).

MONOMERIC INSULIN ANALOG FORMULATIONS

This application is a continuation of application Ser. No. 08/414,880, filed on Mar. 31, 1995 now abandoned,

Field of Invention

The present invention relates to monomeric analogs of human insulin. More specifically, the present invention relates to various parenteral formulations of a monomeric analog having a protracted effect. The formulations provide a prolonged duration of action.

BACKGROUND OF THE INVENTION

It has been known for many years that insulin can be successfully co-crystallized with zinc ions to obtain numerous types of stable crystals with longer time actions than soluble or amorphous, uncrystallized insulin. In the early 1950s, a new formulation of beef insulin crystals was developed which contained only insulin and zinc in an acetate buffer at neutral pH. Hallas-Møller, et al., Science 116, 394–398 (1952). This insulin preparation avoided phosphate ions, which interact strongly with zinc ions to form insoluble zinc phosphate derivatives. Formulations containing only the crystalline insulin in acetate buffer are called Ultralente. Crystals prepared in this manner will be referred herein as Ultralente crystals.

Recently, monomeric insulin analogs have been developed that retain the biological activity of native human insulin but are less prone to dimerization and self-association to higher molecular weight forms. This lack of self-association results in a comparatively more rapid onset of activity. These insulin analogs provide a rapid absorption to place injection time and peak action of insulin into closer proximity with postprandial glucose excursion associated in the response to a meal.

The present invention provides formulations of a monomeric insulin analog that have a protracted effect. Because monomeric insulin analogs do not aggregate and associate like insulin, it is quite remarkable that stable, analog crystals may be formed. Surprisingly, the formulations of the present invention offer a predictable, extended duration of action.

SUMMARY OF THE INVENTION

This invention provides a parenteral pharmaceutical formulation having a protracted effect, consisting essentially of a sterile aqueous suspension of about 20 U/mL to about 500 U/mL insulin analog, about 5 mg/mL to about 10 mg/mL sodium chloride, about 0.2 to about 2.0 mg/mL physiologically acceptable buffer, a zinc ion content of about 0.04 mg/mL to about 20.0 mg/mL, and a physiologically acceptable preservative at a pH of about 6.5 to about 7.8; such that less than 5% of the analog present in the suspension is in the dissolved state.

The invention further provides an insulin analog crystal, prepared by precipitating crystals from a solution consisting essentially of about 200 to about 1200 U/mL insulin analog, about 50 mg/mL to about 100 mg/mL sodium chloride, about 2.0 to about 20.0 mg/mL physiologically acceptable buffer, and a molar excess of zinc ions at a pH of about 5.0 to about 6.0.

DETAILED DESCRIPTION AND PREFERRED EMBODIMENTS

All amino acid abbreviations used in this disclosure are those accepted by the United States Patent & Trademark Office as set forth in 37 C.F.R. § 1.822(b) (2).

The term "insulin analog" or "monomeric insulin analog" as used herein is an insulin analog that is less prone to dimerization or self-association than human insulin. Monomeric insulin analog is human insulin wherein Pro at position $B^{28}$ is substituted with Asp, Lys, Leu, Val, or Ala, and Lys at position $B^{29}$ is Lysine or Proline; des($B^{28}$–$B^{30}$); or des($B^{27}$). Monomeric insulin analogs are described in Chance et al., U.S. patent application Ser. No. 07/388,201, (EPO publication number 383 472), and Brange et al., EPO publication 214 826, and are herein incorporated by reference.

One skilled in the art would recognize that other modifications to the monomeric insulin analog are possible. These modifications are widely accepted in the art and include replacement of the Phenylalanine residue at position $B^1$ with Aspartic acid; replacement of the threonine residue at position $B^{30}$ with Alanine; replacement of the serine residue at position $B^9$ with Aspartic acid; deletion of amino acids at position $B^1$ alone or in combination with a deletion at position $B^2$; and deletion of threonine from position $B^{30}$. Particularly preferred monomeric insulin analogs are Lys$^{B28}$Pro$^{B29}$-human insulin ($B^{28}$ is Lys; $B^{29}$ is Pro) and Asp$^{B28}$-human insulin ($B^{28}$ is Asp).

The term "Ultralente insulin" means formulations containing insulin crystals prepared in acetate buffer in substantial accordance with the teaching of Hallas-Møller, et al., Science 116, 394–398 (1952). Crystals prepared in this manner will be referred to here as Ultralente insulin crystals.

The term "insulin analog crystals" refers to insulin analog crystals prepared by the process described herein.

The term "U" refers to the standard international unit of insulin activity.

The term "substantially" as used herein means greater than about 95%, preferably 98%. For example, substantially crystalline means greater than 95% crystalline material.

The term "treating," as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "physiologically tolerated preservative" is m-cresol, methylparaben, resorcinol, phenol, or other preservative accepted in the art.

The term "physiologically tolerated buffer" is known in the art. Physiologically tolerated buffers include sodium or ammonium acetate or other buffer that does not strongly interact with zinc.

The term "zinc ion" is understood to one skilled in the art. The source of the zinc ion is preferably a zinc salt Representative examples of zinc salts include zinc acetate, zinc bromide, zinc chloride, zinc fluoride, zinc iodide and zinc sulfate. The skilled artisan will recognize that there are many other zinc salts which also might be used in the production of the formulations of the present invention.

As noted above, the invention provides insulin analog crystals and formulations of an insulin analog having a protracted effect. Insulin analog crystals are prepared by precipitating crystals from a solution consisting essentially of about 200 to about 1200 U/mL insulin analog, about 50 mg/mL to about 100 mg/mL sodium chloride, about 2.0 to about 20.0 mg/mL physiologically acceptable buffer, and a molar excess of zinc ions at the isoelectric pH of the analog, generally a pH of about 5.0 to about 6.0

Preferably, insulin analog crystals are prepared by precipitating crystals from a solution consisting essentially of about 400 to about 1000 U/mL insulin analog, about 65 mg/mL to about 75 mg/mL sodium chloride, 5.0 to about 10.0 mg/mL sodium acetate, and about 0.1 mg/mL to about 0.5 mg/mL zinc ions at a pH of about 5.5 to about 5.9. Most preferably, insulin analog crystals are prepared by precipitating crystals from a solution consisting essentially of a 400 U/mL insulin analog, about 70 mg/mL sodium chloride, about 8.0 mg/mL sodium acetate, and 0.15 mg/mL of zinc ions at a pH of about 5.5 to about 5.6.

The crystals form when the pH is adjusted to the isoelectric point of the analog. The pH is adjusted to 5.0 to 6.0 from a more acidic pH by adjusting the basicity of the solution with a physiologically tolerated base such as sodium hydroxide. Likewise, the pH is adjusted to 5.0 to 6.0 from a more basic pH by adjusting the acidity of the solution with a physiologically tolerated acid such as hydrochloric acid.

Preferably, two solutions are prepared that, when combined, produce a solution consisting essentially of about 200 to about 1200 U/mL insulin analog, about 50 mg/mL to about 100 mg/mL sodium chloride, about 2.0 to about 20.0 mg/mL physiologically acceptable buffer, and a molar excess of zinc ions at the isoelectric pH of the analog. The first solution, hereinafter the insulin analog section, comprises about 300 U/mL to about 2000 U/mL insulin analog and a molar excess of zinc ion at an acidic pH of about 2.0 to about 3.0. The second solution, hereinafter the buffer section, comprises about 130 mg/mL to about 270 mg/mL sodium chloride, about 5.0 to about 55.0 mg/mL physiologically acceptable buffer at a basic pH of about 10.5 to about 12.5. Upon combining, the pH of the solutions equilibrate to the isoelectric point of the analog, pH of about 5.0 to 6.0. The crystals precipitate from the solution. This solution is hereinafter referred to as crystal section.

At a pH of about 5.0 to 6.0, crystals precipitate with stirring in about 6 to 72 hours. However, the exact time for complete crystal growth is dependent upon the analog selected and on the conditions employed. The claimed crystals formed are well-defined and rhombohedral in shape.

Preferably, seed crystals are added to the solution to produce a more uniform size distribution of crystalline material and to accelerate the crystallization. The preparation of seed crystals is known in the art and may be derived from human insulin, beef insulin, pork insulin, or insulin analog.

Because monomeric insulin analogs do not self-associate, the physical properties and characteristics of the analog are not analogous to insulin. For example, various monomeric analogs have little, or no, Zn-induced association. This differs dramatically from insulin, which is almost exclusively in a hexamer conformation in the presence of zinc. Because at least two zinc atoms are required to be complexed within each insulin hexamer to form the proper Ultralente insulin crystal, it is quite surprising that insulin analog crystals are formed under conditions analogous to the conditions used to prepare Ultralente insulin.

In addition, the present crystals are preferably prepared in the presence of low levels of phenol, about 500 to 3000 ppm. Because preservative binding, which occurs at molar ratios, drives analog self-association, it is surprising that the crystallization occurs with the monomeric analog in the absence of high preservative concentration. Accordingly, the formation of crystals is unexpected because of the limited tendency of monomeric analogs to form hexamers. This is in contrast to insulin, which readily forms hexamers in the presence of zinc without preservative.

Moreover, it is known in the art that phenolic preservatives compromise Ultralente crystallizations. Therefore, it is surprising that analog crystals form with phenolic preservative present under the conditions described herein.

The present invention further provides formulations of insulin analog crystals suitable for treating diabetes by subcutaneous injection. A parenteral pharmaceutical formulation consists essentially of a sterile aqueous suspension of about 20 U/mL to about 500 U/mL insulin analog, about 5 mg/mL to about 10 mg/mL sodium chloride, 0.2 to about 2.0 mg/mL physiologically acceptable buffer, a zinc ion content of about 0.04 mg/mL to about 20.0 mg/mL, and a physiologically acceptable preservative at a pH of about 6.5 to about 7.8; such that less than 5% of the analog present in the suspension is in the dissolved state. Preferably, less than 2% of the analog in the formulation is in the dissolved state.

The insulin analog formulations described herein are prepared by techniques recognized in the art for the preparation of human insulin ultralente formulations. The insulin analog crystalline suspension is diluted with a dilution solution comprising a physiologically tolerated buffer, and a preservative. The pH of the formulation is adjusted to about 7.3 to about 7.4

The claimed insulin analog formulations result in a slow absorption of analog such that, if desired, no more than one injection per day needs to be administered.

The formulations contain a preserving agent, such as methylparaben, and have a zinc content of about 0.04 to about 20.0 mg/mL at a pH from about 7.1 to about 7.5. The sodium chloride present in the crystals serves as the isotonicity agent. However, one skilled in the art would recognize that, if necessary, the isotonicity of the formulation may be adjusted with sodium chloride or other isotonicity agent known in the art such as glycerin. Additionally, the skilled artisan will recognize that many other preservatives are available for use in the present invention. In preferred embodiments, the total zinc concentration is about 0.04 mg/mL to about 0.1 mg/mL, preferably 0.08 mg/mL for a U40 formulation, and about 0.1 mg/mL to about 0.24 mg/mL, preferably 0.14 mg/mL for a U100 formulation.

The pH of the formulation may be buffered with a physiologically tolerated buffer. Physiologically tolerated buffers include sodium acetate or other buffer which does not strongly interact with zinc.

Most significantly, the time action of the formulation is extended further by adding additional zinc to the formulation so that the total zinc concentration is about 0.5 to about 20 mg per 100 units, preferably about 0.5 mg to about 7 mg per 100 units of insulin. The additional zinc is added after complexation and formulation of the crystals. Zinc fortified formulations have greater than 50% of the total zinc in the formulation in the soluble fraction rather than complexed with the insulin. The pH of the zinc fortified formulation is generally 6.0 to 7.4

The invention further provides insulin analog formulations, consisting essentially of a mixture of crystalline and amorphous material, a Lente-like formulation; as well as exclusively an amorphous formulation, semiLente-like formulation. These mixtures provide a predictable duration of action with a more rapid clearance. In addition, the formulations provide a longer duration of action than soluble insulin analog.

The specific crystallization conditions described herein produce exclusively crystalline preparations. If the conditions are modified, various amounts of non-crystalline, amorphous material are produced. In general, removal of the halide from the buffer section or crystallizing at neutral pH instead of at the isoelectric point will produce non-crystalline material. Preferably a combination of these changes are used to prepare an amorphous product to ensure complete production of amorphous material. Because each monomeric analog will have slightly different optimal conditions for producing exclusively crystalline product, one skilled in the art would appreciate that other procedures or conditions for preparing amorphous material are operable. For example, inclusion of buffer with strong affinity for zinc ions will disrupt the crystallization.

Preferably, a concentrated amorphous zinc analog suspension is prepared by precipitating amorphous zinc-insulin analog particles from a solution consisting essentially of about 200 U/mL to about 1200 U/mL insulin analog, about 2.0 to about 20.0 mg/mL physiologically acceptable buffer, about 50.0 mg/mL to about 100 mg/mL sodium chloride, and a molar excess of zinc ions at a pH of about 7.0 to about 7.5

A semiLente-like analog formulation is prepared by diluting the concentrated suspension of amorphous zinc-insulin analog to yield an amorphous formulation, consisting essentially of about 20 U/mL to about 500 U/mL insulin analog, about 5 mg/mL to about 10 mg/mL sodium chloride, 0.2 to about 2.0 mg/mL physiologically acceptable buffer, a zinc ion content of about 0.07 mg/mL to about 20.0 mg/mL, and a physiologically acceptable preservative at a pH of about 6.5 to about 7.8; such that less than 5% of the analog present in the suspension is in the dissolved state.

A Lente-like insulin analog formulation is a mixture of 70% crystalline and 30% amorphous material. The crystalline portion is prepared in the manner described herein for insulin analog crystals. The amorphous material is prepared as described for semilente-like insulin analog. The crystalline and amorphous portions are combined using conventional techniques.

The insulin analog of the present invention can be prepared by any of a variety of recognized peptide synthesis techniques including classical (solution) methods, solid phase methods, semi-synthetic methods, and more recent recombinant DNA methods.

The following examples are provided merely to further illustrate the preparation of the insulin analogs and the invention. The scope of the invention is not construed as merely consisting of the following examples.

PREPARATION 1

Preparation of Seed

The preparation methodology for Lente seed crystals is known in the art, as described in Jorgan Schlictkrull, "Insulin Crystals: IV. The Preparation of Nuclie, Seeds and Monodisperse Insulin Crystal Suspensions," *Acta Chemica Scandinavica*, 11:299–302 (1957).

EXAMPLE 1

Preparation of Monomeric Analog Crystals
$Lys^{B28}Pro^{B29}$-human insulin section:

To a tarred beaker containing a magnetic stir bar was added 1.034 g of $Lys^{B28}Pro^{B29}$-human insulin crystals (endogenous zinc content of 0.51%, phenol concentration 939 ppm). The crystals were suspended in approximately 30 mL of Milli-Q™ water. A 0.464 mL aliquot of a 10 mg/mL acidic zinc oxide solution was added to the solution to make the total zinc quantity 4.64 mg. The pH was adjusted to 2.77 using 10% hydrochloric acid. After the solution was completely clarified, Milli-Q™ water was added to bring the final weight of the solution to 40 g. The final analog solution (hereinafter analog section) was filtered through a 0.22 µm filter (Millipore Sterivex™-GV Filter Unit).
Buffer section:

To a tarred beaker containing a magnetic stir bar was added 0.565 g of sodium acetate, 4.947 g and sodium chloride. Approximately 25 g of Milli-Q™ water was used to dissolve the salts, and the pH was adjusted to about 11 with 10% sodium hydroxide. After the pH adjustment the solution was brought to a final mass of 30 g using Milli-Q™ water. This solution (hereinafter buffer solution) was filtered through a 0.22 µm filter (Millipore Sterivex™-GV Filter Unit). The buffer solution was adjusted to a pH of 12.01 using 0.25 mL of 10% sodium hydroxide to result in a pH of 5.6 upon combination with the analog solution.
Crystallization:

The following conditions were used to prepare 50 mL of 400 U/mL of crystals (hereinafter crystal section). To a crystallization vessel was added 29.716 mL of analog section. With stirring, a total of 18.75 mL of the buffer section was then added to the vessel. After waiting 60 seconds, 1.544 mL of a human insulin seed mixture (functionality =4) figured at ½ functionality multiplied by grams of analog was added to the vessel. Stirring was continued at ambient temperature for 24 hours.

EXAMPLE 2

Pharmaceutical Preparation of Insulin Analog Having a Protracted Effect (40 U/mL)
Dilution Solution:

A methylparaben stock solution (2 mg/g) was prepared by dissolving 0.6 g of methylparaben in Milli-Q™ water to a final mass of 300 g. To a tarred beaker with a magnetic stir bar was added 277.78 g of the methylparaben stock solution, 0.444 g of sodium acetate, and 4.785 mL of a 10 mg/mL acidic zinc oxide solution. The pH of the solution was adjusted to 5.53 using 10% sodium hydroxide. Milli-Q™ water was added to bring the final mass of the solution to 500 g, and the solution was finally passed through a 0.22 µm filter (Millipore Sterivex™-GV Filter Unit).
Formulation:

A 0.020 mL aliquot of 10% hydrochloric acid and a 0.750 mL aliquot of 10% sodium hydroxide was added to the dilution solution to make the pH 7.72, such that the combination of the crystal section and dilution solution resulted in a final pH of 7.3–7.4 To a tarred container with a magnetic stir bar was added 360 g of the dilution solution (figured at 90% of final volume, specific gravity=1.000) and then 42.40 g of crystal section (figured at 10% of final volume, specific gravity =1.060). A final pH adjustment from 7.27 to 7.34 was made using 0.010 mL of 10% sodium hydroxide.

EXAMPLE 3

Characterization of Crystals and Final Formulation $Lys^{B28}Pro^{B29}$-human insulin crystals prepared as described herein were examined by microscopy and found to contain predominantly rhombohedral crystals approximately 10 µm in size after the 24 hour crystallization time. The final 40 U/mL $Lys^{B28}Pro^{B29}$-human insulin formulation was examined by microscopy and also assayed by a number of analytical tests to verify the preparation and process outcome. Microscopic evaluation indicated the presence of rhombohedral crystals in the formulation. A 1 mL aliquot of the thoroughly resuspended formulation was centrifuged for 30 minutes at 14,000 RPM. The supernatant was carefully removed, and to 800 μL was added 1 μL of 9.6 M hydrochloric acid. A 20 μL aliquot of this mixture was then injected onto an HPLC system running a reversed-phase method. The results from this assay indicated that the supernatant contained 0.034 U/mL of uncrystallized $Lys^{B28}Pro^{B29}$-human insulin. The total potency of the formulation was determined by acidifying 1 mL of the resuspended preparation with 3 μL of 9.6 M hydrochloric acid, and then diluting the sample to 5 mL with 0.01 M hydrochloric acid. A 20 μL aliquot of the sample was injected onto an HPLC system running a reversed-phase method. The total potency was found to be 43.6 U/mL. The purity of the formulation was determined by reversed-phase chromatography by direct injection of 20 μL of an acidified (3 μL 9.6 M hydrochloric acid) 1 mL aliquot of the sample. The purity was determined to be 98.3% on a peak versus total basis. High molecular weight polymer content was determined using size exclusion HPLC by direct injection of 20 μL of the acidified 1 mL aliquot. The total polymer level was 0.17% on a peak versus total basis.

EXAMPLE 4

In Vitro Dissolution Assay

This procedure is a modification of a published assay found in Graham and Pomeroy, *J. Pharm. Pharmacol.* 36, 427–430 (1983). The method, which is accepted in the art as being predictive of biological response, uses the rate of crystal dissolution after a significant dilution with a non zinc-binding buffer as a way of predicting the rate at which the crystalline formulation will dissolve after subcutaneous injection in animals.

The crystalline $Lys^{B28}Pro^{B29}$-human insulin (40 U/mL) preparation (LysPro in Table 1) was tested against Humulin™ Ultralente and two 40 U/mL human insulin Lente formulations. Portions (0.2 mL) of these suspensions were each added to 20 mL of a 0.1 M Tris (tris hydroxymethyl amino methane, Mallinckrodt, Paris, KY) pH 7.5 buffer being stirred at ambient temperature in a glass beaker. At times of 0.5, 3 and 8 hours, 0.2 mL aliquots of the stirred samples were removed and passed through a 0.2 μm Acrodisc® filter. The amount of insulin in the filtrate was quantitated by reversed-phase HPLC. Maximal insulin content was determined by initially assaying an unfiltered, acidified aliquot. Data are reported as percent of maximal insulin for each sample.

TABLE 1

Time-Dependent In Vitro Dissolution Assay

| Sample | Time (hours) | | |
|---|---|---|---|
| | 0.5 | 3 | 8 |
| Humulin ™ Ultralente | 17.7% | 51.0% | 90.4% |
| Humulin ™ Lente, 1 | 43.0% | 74.9% | 98.2% |
| Humulin ™ Lente, 2 | 45.6% | 61.7% | 80.1% |
| LysPro crystals | 26.0% | 67.6% | 95.0% |

The results in Table 1 demonstrate that the dissolution properties $Lys^{B28}Pro^{B29}$-human insulin crystals possess an extended duration of action.

EXAMPLE 5

Preparation of $Lys^{B28}Pro^{B29}$-Human Insulin Crystals

Crystalline Suspension for U400 $Lys^{B28}Pro^{B29}$-Human Insulin Section:

To a tarred beaker containing a magnetic stir bar was added 1.048 g of zinc and less than 500 ppm $Lys^{B28}Pro^{B29}$-hI (phenol concentration was undetectable). The crystals were suspended in approximately 30 mL of water, and a 0.942 mL aliquot of a 10 mg/mL acidic zinc oxide solution was added. The pH was adjusted to 2.6 using 10% hydrochloric acid and 10% sodium hydroxide. After the solution completely clarified, water was added to bring the final weight of the solution to 38.95 g. The final solution was filtered through a 0.22 μm filter (Millipore Sterive™-GV Filter Unit).

Buffer Section:

To a tarred beaker containing a magnetic stir bar was added 0.565 g of sodium acetate, and 4.947 g of sodium chloride. Approximately 25 g of water was used to dissolve the salts, and the pH was adjusted to about 11.52 with 10% sodium hydroxide. After the pH adjustment the solution was brought to a final mass of 30 g with water. The final solution was filtered through a 0.22 μm filter (Millipore Sterivex™-GV Filter Unit).

Crystallization:

Trial combinations of the $Lys^{B28}Pro^{B29}$-hI and buffer sections (0.75 mL of $Lys^{B28}Pro^{B29}$-hI section and 0.45 mL buffer section) were made to determine the correct pH of the buffer section required to achieve a pH between 5.5–5.6 for the final crystallization condition. The buffer section was adjusted to a pH of 12.13 using 0.28 mL of 10% sodium hydroxide to result in a pH of 5.6 upon combination with the $Lys^{B28}Pro^{B29}$-hI section. The following conditions were used to prepare 50 mL of 400 U/mL UltaLente $Lys^{B28}Pro^{B29}$-human insulin (crystal section). To a crystallization vessel was added 30.61 g of $Lys^{B28}Pro^{B29}$-human insulin section figured at $Lys^{B28}Pro^{B29}$-human insulin section plus seed equals 62.5% of the crystal section volume. With stirring, a total of 18.75 mL of the buffer section figured at 37.5% of crystal section was then added to the vessel. After waiting 60 seconds, 0.824 mL of a human insulin seed mixture (functionality=2) figured at ½ functionality multiplied by grams of $Lys^{B28}Pro^{B29}$-hI was added to the crystal section. Stirring was continued at ambient temperature for 48 hours.

The suspension was examined by microscopy (600× magnification) after 48 hours and found to contain a mixture of well defined rhombohedral crystals, poorly formed crystals and amorphous material.

EXAMPLE 6

Preparation of $Lys^{B28}Pro^{B29}$-Human Insulin Amorphous Precipitate $Lys^{B28}Pro^{B29}$-Human Insulin Section:

To a tarred beaker containing a magnetic stir bar was added 0.994 g of zinc containing $Lys^{B28}Pro^{B29}$-hI crystals (endogenous zinc 0.43%, phenol concentration 2663 ppm). The crystals were suspended in approximately 30 mL of water, and a 0.515 mL aliquot of a 10 mg/mL acidic zinc oxide solution was added to the solution. The pH was adjusted to 3.6 using 0.220 mL of 10% hydrochloric acid. After the solution was completely clarified, water was added to bring the final weight of the solution to 40 g. The final solution was filtered through a 0.22 μm filter (Millipore Sterivexm™-GV Filter Unit).

Buffer Section:

To a tarred beaker containing a magnetic stir bar was added 0.565 g of sodium acetate, 4.947 g and sodium chloride. Approximately 25 g of water was used to dissolve the salts, and the pH was adjusted to about 12.6 with 10% sodium hydroxide. After the pH adjustment, water was added to achieve a final mass of 30 g and the solution was filtered through a 0.22 μm filter (Millipore Sterivex™-GV Filter Unit).

Amorphous Suspension:

Trial combinations of the $Lys^{B28}Pro^{B29}$-hI and buffer sections (0.75 mL of $Lys^{B28}Pro^{B29}$-hI section and 0.45 mL buffer section) were made to determine the correct pH of the buffer section required to achieve a pH between 7.2–7.4 for the final solution. Additional 10% HCl was added to the buffer section to adjust the pH to 12.2 The final combination solution contained 31.25 mL of the $Lys^{B28}Pro^{B29}$-hI section and 18.75 mL of the buffer section at pH 7.3. Stirring was continued at ambient temperature for 24 hours.

The suspension was examined by microscopy (600× magnification) after 48 hours and found to contain exclusively amorphous material.

EXAMPLE 7

Crystalline and Amorphous mixed Preparation

To prepare a Lente-like formulation 70% of a crystalline $Lys^{B28}Pro^{B29}$-hI suspension of Example 1 is mixed with 30% of amorphous $Lys^{B28}Pro^{B29}$-hI suspension of Example 6.

We claim:

1. A parenteral pharmaceutical formulation having a protracted effect, consisting essentially of a sterile aqueous suspension of about 20 U/mL to about 500 U/mL $Lys^{B28}Pro^{B29}$-human insulin analog, about 5 mg/mL to about 10 mg/mL sodium chloride, about 0.2 to about 2.0 mg/mL physiologically acceptable buffer, a zinc ion content of about 0.04 mg/mL to about 20.0 mg/mL, and a physiologically acceptable preservative at a pH of about 6.5 to about 7.8; such that less than 5% of the analog present in the suspension is in the dissolved state, provided that if the formulation contains crystalline material the crystals are rhombohedral crystals and if m-cresol, resorcinol or phenol are present the concentration is less than 3,000 ppm.

2. A formulation of claim 1, wherein the buffer is sodium acetate.

3. A formulation of claim 2, wherein analog present in suspension is at least 95% crystalline material.

4. A formulation of claim 3, wherein the zinc ion content is about 0.04 mg/mL to about 0.24 mg/mL.

5. A formulation of claim 4, wherein the zinc ion content is about 0.08 mg/mL.

6. A formulation of claim 4, wherein the zinc ion content is about 0.14 mg/mL.

7. A parenteral pharmaceutical formulation of claim 5 wherein: the insulin analog concentration is about 40 U/mL insulin analog, sodium chloride concentration is about 7 mg/mL sodium chloride, the concentration of sodium acetate is about 1.6 mg/mL sodium acetate, and the pH is about pH 7.0 to about pH 7.4.

8. A parenteral pharmaceutical formulation of claim 6 wherein: the insulin analog concentration is about 100 U/mL insulin analog, sodium chloride concentration is about 7 mg/mL sodium chloride, the concentration of sodium acetate is about 1.6 mg/mL sodium acetate, and the pH is about pH 7.0 to about pH 7.4.

9. A formulation of claim 1, wherein analog present in suspension is at least 95% amorphous material.

10. A formulation of claim 1, wherein analog present in suspension is about 70% crystalline and about 30% amorphous material.

11. An insulin analog crystal, prepared by precipitating crystals from a solution consisting essentially of about 200 to about 1200 U/mL $Lys^{B28}Pro^{B29}$-human insulin analog, about 50 mg/mL to about 100 mg/mL sodium chloride, about 2.0 to about 20.0 mg/mL physiologically acceptable buffer, and a molar excess of zinc ions at a pH of about 5.0 to about 6.0; provided that such crystals are rhombohedral.

12. An insulin analog crystal of claim 11, wherein the physiologically acceptable buffer is sodium acetate.

13. An insulin analog crystal of claim 12, wherein the zinc ion concentration is about 0.1 to about 0.5 mg/mL.

14. An insulin analog crystal, prepared by combining: A first solution consisting essentially of about 300 U/mL to about 2000 U/mL $Lys^{B28}Pro^{B29}$-human insulin analog, and a molar excess of zinc ion at a pH from about 2.0 to about 3.0; and A second solution consisting essentially of about 130 mg/mL to about 270 mg/mL sodium chloride, about 5.0 to about 55.0 mg/mL physiologically acceptable buffer at a pH from about 10.5 to 12.5; such that the pH of the combined solutions is pH 5.0 to ph 6.0; provided that such crystals are rhombohedral.

15. A process of preparing $Lys^{B28}Pro^{B29}$-human insulin crystals, comprising:

Combining a first solution consisting essentially of about 300 U/mL to about 2000 U/mL insulin analog, and a molar excess of zinc ion at a pH from about 2.0 to about 3.0; and a second solution consisting essentially of about 130 mg/mL to about 270 mg/mL sodium chloride, about 5.0 to about 55.0 mg/mL physiologically acceptable buffer at a pH from about 10.5 to 12.5; such that the pH of the combined solutions is pH 5.0 to pH 6.0; provided that such $Lys^{B28}Pro^{B29}$-human insulin crystals are rhombohedral.

16. The process of claim 15, which further comprises:
Adding seed crystals.

* * * * *